US005367002A

United States Patent [19]
Huang et al.

[11] Patent Number: 5,367,002
[45] Date of Patent: Nov. 22, 1994

[54] DENTAL COMPOSITION AND METHOD

[75] Inventors: Chin-Teh Huang, Dover; Paul D. Hammesfahr, Wyoming; Steven R. Jefferies, Milford, all of Del.

[73] Assignee: Dentsply Research & Development Corp., Milford, Del.

[21] Appl. No.: 832,202

[22] Filed: Feb. 6, 1992

[51] Int. Cl.$^5$ ................................................. C08K 3/40
[52] U.S. Cl. ..................................... 523/116; 523/115; 523/117; 523/118
[58] Field of Search ................ 523/116, 115, 117, 118

[56] References Cited

U.S. PATENT DOCUMENTS

| | | | |
|---|---|---|---|
| 3,709,866 | 1/1973 | Waller | 260/27 R |
| 3,825,518 | 7/1974 | Foster et al. | 260/42.52 |
| 4,222,780 | 9/1980 | Shibatani et al. | 106/35 |
| 4,235,633 | 11/1980 | Tomioka et al. | 106/35 |
| 4,259,117 | 3/1981 | Yamauchi et al. | 106/35 |
| 4,362,889 | 12/1982 | Bowen | 560/221 |
| 4,368,043 | 1/1983 | Yamauchi et al. | 433/217 |
| 4,499,251 | 2/1985 | Omura et al. | 526/276 |
| 4,500,657 | 2/1985 | Kumar | 523/116 |
| 4,514,342 | 4/1985 | Billington et al. | 260/952 |
| 4,525,256 | 6/1985 | Martin | 204/159.18 |
| 4,539,382 | 9/1985 | Omura et al. | 526/276 |
| 4,553,940 | 11/1985 | Koblitz et al. | 523/115 |
| 4,645,456 | 2/1987 | James | 433/217.1 |
| 4,657,941 | 4/1987 | Blackwell et al. | 522/14 |
| 4,719,149 | 1/1988 | Aasen et al. | 428/473 |
| 4,816,495 | 3/1989 | Blackwell et al. | 522/14 |
| 4,872,936 | 10/1989 | Engelbrecht | 156/307.3 |
| 4,880,660 | 11/1989 | Aasen et al. | 427/2 |
| 4,920,188 | 4/1990 | Sakashita et al. | 526/198 |
| 4,966,934 | 10/1990 | Huang et al. | 524/315 |
| 5,063,257 | 11/1991 | Akahane et al. | 523/116 |

FOREIGN PATENT DOCUMENTS

| | | |
|---|---|---|
| 1069239 | 1/1980 | Canada . |
| 1134532 | 10/1982 | Canada . |
| 1158383 | 12/1983 | Canada . |
| 1159984 | 1/1984 | Canada . |
| 1189996 | 7/1985 | Canada . |
| 1202441 | 3/1986 | Canada . |
| 1225489 | 8/1987 | Canada . |
| 1243796 | 10/1988 | Canada . |
| 1244177 | 11/1988 | Canada . |
| 1245437 | 11/1988 | Canada . |
| 1262981 | 11/1989 | Canada . |
| 0219058 | 4/1987 | European Pat. Off. . |
| 0241277 | 10/1987 | European Pat. Off. . |
| 0323120 | 7/1989 | European Pat. Off. . |
| 0391619 | 10/1990 | European Pat. Off. . |
| 0395427 | 10/1990 | European Pat. Off. . |
| 51-123258 | 10/1976 | Japan . |

OTHER PUBLICATIONS

Glass-Ionomer Cement by Wilson et al pp. 21, 22 and 25-27, 1988.
New Glass Ionomer Composite Resin Hybrid Restorative, Journal of Dental Research, Abstracts of papers vol. 66 #51 Mar. 11-15, 1987.
Properties of a glass-ionomer/resin-composite hybrid material, Dental Materials pp. 355-358, Sep. 1989.

*Primary Examiner*—Edward J. Cain
*Attorney, Agent, or Firm*—Dale R. Lovercheck; Edward J. Hanson, Jr.

[57] ABSTRACT

The invention provides dental composite compositions formed by mixing a curable liquid composition with a powder in preselected proportions. The composite compositions formed are useful as cement, liner, base, restorative, pit and fissure sealants, and/or core build-up material, etc. having improved adhesion to dentin. These composite compositions include polyalkenoic acid, filler which provides elutable cations which are reactive with the polyalkenoic acid and fluoride ion, water to provide for elution of cations reactive with polyalkenoic acid, polymerizable monomer and/or prepolymer composition, unsaturated organic acid having 1 or more polymerizable groups and a catalyst system for polymerization. Optionally the composites include inert reinforcing filler for strength, aesthetics, and radiopacity.

48 Claims, No Drawings

DENTAL COMPOSITION AND METHOD

The invention relates to dental composite compositions. In particular the invention provides dental composite compositions which polymerize in-situ by reaction between polymerizable monomers and/or prepolymers, a polyalkenoic acid, polyvalent cations, and an acid functional polymerizable organic compound. Dental composite compositions in accordance with the invention include cement, liner, base, restorative, core build-up material and pit and fissure sealants formed by mixing a curable liquid in preselected proportions with a powder containing glass.

Foster, Waller and Koblitz et al in U.S. Pat. Nos. 3,825,518; 3,709,866 and 4,553,940 each assigned to Dentsply and incorporated herein by reference, disclose dental composites comprised of polymerizable ethylenically unsaturated monomer or prepolymer, and an inert filler material which serves to reduce the polymerization shrinkage. Dental glass ionomers are disclosed by Wilson et al in Glass-Ionomer Cement pages 21, 22 and 25-27, 1988 as an aqueous solution of a polyalkenoic acid combined with a glass powder containing elutable calcium and aluminum cations mixed with the polyalkenoic acid. The glass powders reinforce the resulting polysalt. Mitra in European Patent Application 0323120 describes modification of polyacrylic acid with methacrylate groups and the addition of water soluble monomer to conventional glass ionomer to improve strength in thin films immediately upon polymerization.

Glass ionomer has been used in clinical dentistry for its advantageous release of fluoride, biocompatibility, and adhesion to dentin, as discussed by Mathes et al at page 355. Mathes et al in Properties of a New Glass Ionomer Composite Resin Hybrid Restorative, Journal of Dental Research, Abstracts of Papers Vol. 66 #51 Mar. 11-15, 1987 and in Properties of a glass-ionomer/resin-composite hybrid material, Dental Materials pages 355-358, September 1989 disclose a dental composition containing glass ionomer and polymerizable monomer. Glass ionomer is formed, for example, by reacting glass such as fluoroaluminum silicate particles, for exampled with polycarboxylic acid. The composition of the present invention has at least about 400% greater bond strength to dentin than the composition of Mathes et al.

Omura et al. in U.S. Pat. No. 4,499,251 discloses adhesive compositions. Kumar in U.S. Pat. No. 4,500,657 discloses dental restorative compositions having improved mechanical properties and hydrolytic stability. Billington et al in U.S. Pat. No. 4,514,342, the disclosure of which is incorporated herein by reference in its entirety, discloses polyethylenically unsaturated monophosphates. Martin in U.S. Pat. No. 4,525,256 discloses a photopolymerizable composition including catalyst comprising diketone plus 4-(N,N-dimethyl-aminobenzoic acid or ester thereof. Blackwell et al. in U.S. Pat. No. 4,657,941, the disclosure of which is incorporated herein by reference in its entirety, discloses a biologically compatible phosphorus containing an adhesion promoter and a sulfinic accelerator. Aasen et al. in U.S. Pat. Nos. 4,719,149 and 4,880,660 discloses a method for priming hard tissue. Blackwell et al. in U.S. Pat. No. 4,816,495 discloses biologically compatible adhesive visible light curable compositions. Engelbrecht in U.S. Pat. No. 4,872,936 discloses polymerizable cement mixtures. Akahane at al in U.S. Pat. No. 5,063,757 disclose dental glass ionomer cement compositions.

Present restorative dental practice using prior art composites requires the elimination of water from the surface of the tooth or teeth being restored to obtain optimum adhesion, since water is immiscible with these compositions and serves as a barrier to intimate contact between the hydrophilic tooth and the hydrophobic restorative material. A "rubber dam" is commonly used to isolate the tooth from the surface moisture of the oral environment including breath and saliva. However, moisture is constantly delivered from within the body and tooth via the dentin tubulae to the surface of the dentin. Although such water is customarily removed by an air syringe, it is almost instantly replenished contaminating the dentin surface. In some cases a rubber dam cannot be employed. Accordingly, the water tolerant compositions of the present invention are particularly advantageous and represent an improvement over conventional dental composite restorative materials.

After a restorative is placed and hardened, it is bonded to the tooth, maintenance of the adhesion to the tooth depends, among other things, on stresses at the interface between the tooth and the filling material. One of the important stress elements is the difference in the coefficient of thermal expansion between the restorative and the filling. The compositions of the invention have reduced coefficients of expansion more nearly matching tooth structure, providing improvement over prior art composite materials.

Because of the rate of elution and reaction of cations and polyalkenoic acid prior art glass ionomer compositions develop strength slowly, (it continues for 24 hours or more), at early stages the glass ionomer materials are particularly subject to dissolution by contaminating moisture from the saliva, and require special precautions and hydrophobic surface coatings of a dental varnish to overcome these inherent difficulties. In contrast the compositions of this invention form useful articles having substantial strength immediately upon polymerization. Compositions may be provided as powders and liquid which are measured and combined before use by mixing on a dental mixing pad with a spatula. Alternatively, components of the composition may be combined in such a manner as to provide a composition consisting of two pastes for convenience in mixing and measuring by separating the mutually reactive components among the two pastes.

BRIEF DESCRIPTION OF THE INVENTION

The invention provides dental composite compositions formed by mixing a curable liquid composition with a powder in preselected proportions. The composite compositions formed are useful as cement, liner, base, restorative, pit and fissure sealants, and/or core build-up material, etc. having improved adhesion to dentin. These composite compositions include polyalkenoic acid, filler which provides elutable cations which are reactive with the polyalkenoic acid and fluoride ion, water to provide for elution of cations reactive with polyalkenoic acid, polymerizable monomer and/or prepolymer composition, unsaturated organic acid having 1 or more polymerizable groups and a catalyst system for polymerization. Optionally the composites include inert reinforcing filler for strength, aesthetics, and radiopacity.

DETAILED DESCRIPTION OF THE INVENTION

In a preferred embodiment, the invention provides a liquid and powder which are mixed in preselected proportions to form dental cement, liner, base, restorative, pit and fissure sealants, and core build-up material. The ratio preferably used is from 0.5 to 6 parts by weight powder to 1 part by weight liquid. Suitable consistencies for dental cement, liner, base, restorative and core build-up material are formed by mixing powder (filler) with a polymerizable liquid containing, for example, dipentaerythritol pentacrylate phosphoric acid ester in various ratios. These mixtures are cured by exposure to visible light. In basing applications the dental compositions are positioned under composite, amalgam, metal and ceramic restorations. Beneficially compositions of the invention bond to tooth structure (i.e. dentin and enamel), release fluoride and are biocompatible.

Water is an important component of the compositions of this invention. Because these compositions contain water, they are tolerant of trace moisture derived from hydrated tissue and moisture present in the oral cavity derived from the breath and saliva. Further, it is important according to this invention, that the polyalkenoic acid, water, polymerizable and/or prepolymer, monomer and acid functional polymerizable organic compound in the concentrations used be mutually soluble in one another at room temperature, i.e. form a homogeneous solution. The compositions of this invention do not rely upon non-reactive surfactants to achieve apparent mutual solubility. Each component of the composition is used at a concentration that forms a homogeneous solution to provide mutual solubility of the components. Thus, mutual solubility of the liquid composition is achieved without the addition of non-reactive surfactants. Preferably the curable compositions of the invention include 0.5 to 30 parts by weight of water, more preferably 0.5 to 20 parts by weight, most preferably 0.5 to 10 parts by weight, of water in the cured composition.

The compositions of the invention have greater strength immediately after placement and after curing than do conventional dental glass ionomer for corresponding uses. The compositions of the invention elute fluoride ion to reduce the solubility of adjacent enamel and dentin and reduce the incidence of secondary caries.

Compositions of the present invention may be light cured to provide filling materials especially useful in Class III and Class V restorations. They are also useful as core build-up materials at high filler solids concentrations with good strength values and insensitivity to trace interfacial water, the combination of which is an improvement in this invention. The compositions of the inventions are especially useful in Class V situations where an erosion lesion is partly or wholly in dentin, the cavity thickness shallow and retention minimal, and the possibility of water contamination exists.

In a preferred embodiment superior resistance to abrasive loss compared to conventional composite has been shown. Abrasion resistance is particularly useful in Class V applications for resisting tooth brush abrasion at the neck of the tooth (where it meets the gingiva).

Compositions of the invention are useful at lower solids (filler) concentration to provide consistencies suitable for use in lining the dentin of prepared dental cavities and as pit and fissure sealants, and at thicker consistencies for use as bases of low solubility and good strength under other filling materials including conventional composites and amalgams. The compositions polymerize rapidly and elute fluoride ions which can react with hydroxyapatite of the tooth to form the less acid-soluble fluorapatite structure to reduce the risk of caries adjacent the filling. Liner compositions in accordance with the invention flow readily and wet dentin easily.

In accordance with an embodiment of the invention, intermediate solids concentrations are provided for adhesive dental cements used under light-transmitting glass-ceramic inlays, crowns, dental veneers, orthodontic brackets, or to fill pits and fissures in teeth according to current dental practice using a light cure catalyst system and/or a redox polymerization catalyst system such as benzoyl peroxide and reducing amine or sulfinate.

Curable compositions of the invention may utilize one or more catalyst systems to cause them to harden promptly. Thus for example, light curable compositions are provided wherein the catalyst system includes 1) a light sensitizer, for example camphorquinone or methyl benzoin ether, causes polymerization to be initiated upon exposure to activating wavelengths of light; and 2) a reducing compound, for example a tertiary amine such as ethyl 4-dimethylaminobenzoate or dimethyl-p-toluidine or an organic sulfinate, for example lithium-p-toluene sulfinate or benzene sulfinic acid. Accelerators for the polymerization for example metal salts such as copper acetylacetonate, phosphinic acids and phosphinates, may also be used. A room temperature activating catalyst system comprised of a redox polymerization system may be employed advantageously with the compositions of the invention by adding, for example, a peroxide capable of producing free radicals when activated by a reducing agent at such temperature. Peroxides useful in the invention include benzoyl peroxide and lauroyl peroxide. Suitable promoters include the same reducing agents and accelerators used in light curing catalyst systems. In a further modification of these systems, it has been found advantageous to include a light initiator, a free radical generating peroxide catalyst, a reducing agent, and optionally, accelerators. Thus, compositions are provided with longer working times before hardening after the components are mixed, and more complete conversion to polymer is achieved using light sensitive initiators. Preferably curable dental compositions of the invention are comprised of 0.01 to 10 parts by weight, more preferably 0.02 to 5 parts by weight, and most preferably 0.03 to 4 parts by weight, of a catalyst system ingredients in the cured composition.

Compositions in accordance with a preferred embodiment of the invention are minimally affected by phosphoric acid gel, cure by exposure to visible curing light, and are radiopaque. They form a protective barrier for dentin and pulp, protecting them from acid containing cements and enamel etching agents. Compositions in accordance with the invention are thermal insulators under restorations. A calcium hydroxide preparation such as Dycal from Dentsply International is preferably placed on pulp exposures before the application thereto of compositions in accordance with the invention.

Preferably curable dental compositions of the invention include 1 to 60 percent by weight, more preferably 2 to 50 percent by weight, most preferably 2 to 40 percent by weight, of an acid functional polymerizable organic compound in the cured composition. In accordance with a preferred embodiment of the invention, liquids contain polymerizable acid functional materials having ethylenic unsaturation include, among others, organic esters of one or more acids of phosphorus (hereinafter referred to as phosphorus acid esters), wherein the organic portion of the ester contains at least one polymerizable ethylenically unsaturated group. The organic portion of the ester may be alkenyl, alkenoxy, cycloalkenyl, aralkenyl, or alkenaryl, and preferably may have from 2 to 40 carbon atoms. The organic portion may be straight chain, branches, or cyclic, can contain skeletal hetero atoms, i.e., atoms other than carbon, and can be unsubstituted or substituted with moieties which do not interfere with the free radical polymerization of the phosphorus acid esters. Examples of unsaturated phosphorus containing acid esters which may be used include, but are not limited to, monomers containing phosphoric acid groups such as hydroxyethyl methacrylate monophosphate, 2,2,-bis($\alpha$-methacryloxy-$\beta$-hydroxy-propoxyphenyl) propane diphosphonate (BIS-GMA diphosphonate), BIS-GMA diphosphate, methacryloxyethyl phosphate, and glyceryl dimethacrylate phosphate. Other suitable polymerizable acid esters are disclosed, for example, in U.S. Pat. No. 4,499,251 to Omura et al, U.S. Pat. No. 4,222,780 to Shibantani et al, U.S. Pat. No. No. 4,235,633 to Tomioka, U.S. Pat. No. 4,259,117 to Yamauchi et al, U.S. Pat. No. 4,368,043 to Yamauchi et al, and Sakashita in U.S. Pat. No. 4,920,188 incorporated herein by reference for such disclosure.

In accordance with a preferred embodiment of this invention, liquids contain polymerizable phosphate acid ester monomers which are reactive with cations eluted from the reactive fillers. Upon polymerization, alone or in combination with other polymerizable components, these form polyacids which are also reactive with cations. Polymerizable phosphates preferred for use with this invention are adhesive to tooth structure and improve the adhesion of the compositions. Liquids according to the invention, including the polymerizable phosphate acid ester monomers and water are acidic, creating a low pH environment in which polymerizable organic esters might be hydrolyzed over time. This can be minimized or overcome by partial neutralization to increase the pH of solutions which result.

In accordance with an embodiment of the composite composition, phosphoric acid esters useful in the composition include:

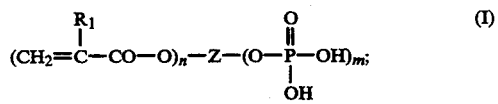

(I)

wherein $R_1$ is hydrogen, lower alkyl of from 1 to 5 carbons, halogen or CN radical; n and m are independently integers of 1 or greater, Z is an aliphatic, cycloaliphatic or aryl radical having a carbon chain comprising at least 2 carbon atoms and 0 or more oxygen or sulfur atoms and having a valency of m+n. In a preferred embodiment of the invention, the phosphoric acid esters used are those compositions of Formula I wherein m is 1.

In accordance with a further embodiment of the invention, acid esters within the scope of Formula I are partially neutralized to form phosphoric acid esters of the general Formula II and III as follows:

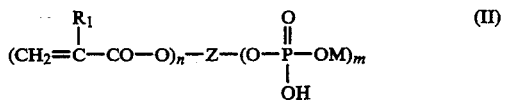

(II)

and

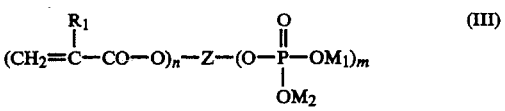

(III)

wherein M, $M_1$ and $M_2$ each is independently a cation, such as K, Li, Na, $NH_4$ or an amine. Preferably 20–40 equivalent weight percent of the phosphoric acid ester is neutralized by reaction with base.

A preferred embodiment of the invention includes a powder and liquid, the powder comprising 20 to 90 parts by weight of a fluoroalumino silicate glass powder having an average particle size of 0.02 to 50 μm, a specific gravity of 2.0 to 4.0 and capable of reacting with the polyalkenoic acid, and 1 to 60 parts nonreactive glass powder; and a liquid comprising 0.5 to 30 parts by weight of a polyalkenoic acid having a weight. average molecular weight of 5,000 to 500,000 (more preferably from 10,000 to 100,000), 0.5 to 30 parts by weight of water, 1 to 60 parts by weight of a polymerizable monomer and/or prepolymer, 1 to 60 parts by weight of an acid functional polymerizable organic compound, for example, dipentaerythritol pentacrylate phosphoric acid and/or salts thereof, 0.01 to 5 parts by weight of a polymerization catalyst, and 0.001 to 5 parts by weight of a reducing agent.

Polyalkenoic acids, as used herein, are identified as organic polymers containing carboxyl or other acid groups reactive to form polysalts with cations eluted from reactive filler. A preferred form of a polyalkenoic acid is a polymer of an $\alpha$-$\beta$ unsaturated carboxylic acid. Such acids include, for example, polymers of acrylic acid, methacrylic acid, 2-chloroacrylic acid, 2-cyanoacrylic acid, aconitic acid, mesaconic acid, maleic acid, itaconic acid, fumaric acid, glutaconic acid, utraconic acid, pentaerythritol triacrylate phosphoric acid ester, dipentaerythritol pentacrylate phosphoric acid ester, ethylene monomethacrylate monosulfate, and their copolymers with other ethylenically unsaturated polymerizable monomers, including without limitation their polymerizable esters, styrene, acrylonitrile, 1,1,6 trimethyl hexamethylene dimethacrylate esters, and the like. It will be understood that a large number of such polyacids may be utilized in accordance with the invention. In a preferred composition of the invention, polyacrylic acid is utilized. Other polyacids may be used to achieve beneficial properties in the final composition such as increased toughness and set time control. Preferably curable dental compositions of the invention include 0.5 to 30 percent by weight, more preferably 0.5 to 20 percent by weight, most preferably 0.5 to 10 percent by weight, of a polyalkenoic acid in the cured composition.

Polymerizable liquids and/or prepolymers are selected to form, in combination with the other ingredients of the liquid composition of the invention, a balance of properties in the liquid prior to polymerization, as well as in the polymerized product. These include mutual solubility, stability, viscosity, mechanical strength and physical integrity of the cured materials, biotolerance, and the like. Monomers useful as polymerizable monomer in accordance with the invention include those disclosed in Dentsply's U.S. Pat. Nos. 3,825,518, 3709,866, 4,553,940, 4,514,342, and 4,657,941 incorporated herein by reference, including ethylene glycol dimethacrylate, triethylene glycol dimethacrylate, dipropylene glycol dimethacrylate, BIS-GMA, 1,1,6 trimethyl hexamethylene urethane dimethacrylate, cyclohexyl methacrylate, hydroxyethyl methacrylate, glycerol mono-, di- and tri-methacrylates. Prepolymers useful in accordance with the invention include adducts formed by the reaction of BIS-GMA and 1,1,6 trimethyl hexamethylene diisocyanate, the adducts formed between polyethers and diisocyanates end capped with hydroxyethyl methacrylate, the adducts formed by polyethers or polyalcohols with an isocyanato methacrylate such as isocyanatoethyl methacrylate. By substituting the methacrylate function of these monomers and prepolymers with the corresponding acrylate, fluoroacrylate, or cyanoacrylate function, additional, polymerizable moities are provided for use as monomers or prepolymers in accordance with the invention. In one preferred example the monomer and/or polymer composition is comprised of triethyleneglycol dimethacrylate and hydroxyethyl methacrylate. Preferably curable dental compositions of the invention include 1 to 60 parts by weight, more preferably 2 to 50 percent by weight, most preferably 5 to 40 percent by weight, of polymerizable monomer and/or prepolymer in the cured composition.

Preferred reactive fillers for use in accordance with the invention include elutable cations having a valence of 2 or more, for example, strontium, calcium, zinc, aluminum, iron, zirconium. Elutable glasses also preferably contain elutable fluoride ion. Fluoride is usually introduced into the glass during melt formation wherein it serves as a flux for preparation of the elutable glasses. Such fillers which provide these elutable fluoride ions and cations reactive with the polyacids include, for example, finely ground aluminosilicate and silicate glasses including, for example without limitation, calcium fluoroaluminosilicate glasses, strontium fluoroaluminosilicates, strontium-calcium fluoroaluminosilicates and the like. Preferably, the filler in dental compositions in accordance with the invention includes strontium aluminosilicate glasses. Preferably curable dental compositions of the invention include 10 to 90 percent by weight, more preferably 20 to 90 percent by weight, most preferably 30 to 90 percent by weight, reactive glass in the cured composition.

As used herein, non-reactive fillers are characterized as those which do not form hardened coherent products within 10 hours by reaction between the glass filler and a 50% aqueous solution of the polyacid after being mixed at a ratio of 2 g powder to 1 gram polyacid solution. Non-reactive fillers are optionally included in compositions of the invention to include beneficial properties. For example, fumed silica is a non-reactive filler which is included to provide viscosity control, and barium aluminosilicate is a non-reactive filler included to extend the composition, and increase its strength and radiopacity. Curable dental compositions in accordance with one embodiment of the invention include preferably 1 to 60 percent by weight, more preferably 4 to 40 percent by weight, most preferably 4 to 30 percent by weight, of the non-reactive filler in the cured composition.

Preferably, both reactive and non-reactive fillers are included having a coating such as an organic phosphate for compatibility with the organic components of the compositions. A suitable organic phosphate is pentaerythritol trimethacrylate phosphate. Alternative coatings, especially for the non-reactive fillers, include organic silane, such as gamma methacryloxy propyl trimethoxy silane applied by procedures well known in the art.

Preferably, compositions in accordance with the invention may be polymerized by redox catalysts to provide dental cements under non-light transmitting restorations, such as crowns prepared from porcelain fused to metal. Preferably, compositions in accordance with the invention are water tolerant to reduce the effects of surface contamination by water which may affect adhesion between tooth and restorative. Preferably, compositions in accordance with the invention more nearly match the coefficient of thermal expansion than do conventional composites to permit greater longevity to the adhesive bond formed. Preferably, compositions in accordance with the invention are radiopaque through the use of an radiopaque non-reactive fillers.

In accordance with a preferred embodiment of the invention, compositions are prepared from powder(s) and liquid which are measured and mixed on a dental mixing pad with a spatula. Alternatively, the components are combined to provide a composition consisting of two pastes. Thus, for convenience in mixing and measuring, the mutually reactive components are divided between two pastes. For example, water in the composition may be combined with the polymerizable unsaturated monomer and/or prepolymer composition and a reactive filler to form one paste; and the polyalkenoic acid, unsaturated organic phosphate ester and non-reactive filler may be combined into another paste. Depending on the particular catalyst system employed, components of the catalyst system are included in one or the other of the pastes to form stable compositions which may be packaged in tubes or syringes for convenience in storage and measurement. When combined, the pastes react without further activation if a redox polymerization system is used, and/or they may be irradiated with intense light, for example, from a MAX dental light polymerization unit (Caulk/Dentsply), if a light sensitive photopolymerization catalyst system is used.

A preferred curable dental composition in accordance with the invention includes polyacrylic acid, hydroxyethyl methacrylate, water, triethyleneglycol dimethacrylate, dipentaerythritol pentacrylate phosphoric acid ester and/or its partial salt, camphorquinone, dimethylamino benzoic acid ester, a free radical inhibitor such as butylated hydroxytoluene, strontium fluoroalumino silicate and, optionally, barium boro alumino silicate glasses.

EXAMPLE 1A

Partially Neutralized Dipentaerythritol Pentacrylate Phosphoric Acid Ester.

Dipentaerythritol Pentacrylate Phosphoric Acid Ester is prepared according to Example 2 of U.S. Pat. No. 4,816,495. A solution of technical dipentaerythritol monohydroxypentacrylate (1 mole) and triethylamine (1 mole) in dry ether is slowly added with stirring to a solution of phosphorus oxychloride (1 mole) in dry ether, at 0° C. After stirring for two hours at room temperature, the triethylamine hydrochloride formed is separated and the product remaining in solution is hydrolyzed by addition of the ether solution to ice water with stirring at below 10° C. The resultant mixture is separated and the separated ether layer is then extracted with a 25% aqueous sodium carbonate solution until the aqueous extract exhibits a pH of 8.0–8.5. The alkaline aqueous extract is mixed with methylene chloride and then acidified with 18% hydrochloric acid to about pH 1. The aqueous phase is discarded. The methylene chloride extract is dried with anhydrous sodium sulfate which is filtered off. The total acid content of the methylene chloride extract is determined by titration. 25 equivalent weight percent of the total acid is neutralized by the addition of a 35% solution of sodium hydroxide in water at temperature less than 23° C., with adequate mixing. The methylene chloride is then removed from the solution under reduced pressure in a rotovap to give the title compound as a clear straw colored oil.

EXAMPLE 1

Polymerizable liquid prepared by mixing 14.2 parts by weight of a 50% aqueous polyacrylic acid solution; 28.5 parts by weight hydroxyethyl methacrylate; 0.1 parts by weight butylated hydroxytoluene; 28.5 parts by weight triethyleneglycol dimethacrylate; 28.5 parts by weight partially neutralized dipentaerythritol pentacrylate phosphoric acid ester prepared as in Example 1A; and 0.2 parts by weight camphorquinone.

EXAMPLE 2

Powder for use with the liquid of Example 1 is formed by adding 79.19 parts by weight strontium aluminosilicate glass; 0.8 parts by weight ethyl 4-dimethylaminobenzoate; 20 parts by weight barium alumino borosilicate glass and 0.01 parts by weight inorganic pigments.

EXAMPLE 3

Powder for use with the liquid of Example 1 is formed by adding 99.19 parts by weight strontium aluminosilicate glass; 0.8 parts by weight ethyl 4-dimethylaminobenzoate; and 0.01 parts by weight blue inorganic pigments.

EXAMPLE 4

A mixture useful as a dental liner is prepared by mixing 1.8 parts by weight of the powder prepared as in Example 2 with 1 part by weight of the polymerizable liquid prepared as in Example 1 on a mixing pad for 30 seconds. The mixture is protected from light until ready to be used. Specimens are prepared for testing using the Caulk MAX curing light. The composition so prepared has a compressive strength of 24,725 psi according to ISO 7489, diametral tensile strength of 4,478 psi according to ADA 27, and flexural strength of 26.9 MPa and flexural modulus of 2,517 MPa according to ISO 4049, and a bond strength to human dentin of 1,302 psi.

Extracted human teeth used for the bond strength testing are treated in 1% sodium hypochlorite for 18 to 24 hours, washed with water, mechanically sanded with 120/320/600 grit carborundum paper until the dentin is exposed. The prepared teeth are stored in distilled water in a refrigerator at about 4° C. until needed. Each tooth is blow dried with compressed dry air to ensure the dentin surface is free from noticeable moisture.

Using a ball tipped applicator, the test compositions are placed on prepared tooth structure. In Examples 6 and 7 the bond strengths are obtained by applying primer (Prisma Universal Bond ® 3 Primer described in U.S. Pat. No. 4,966,934) with a brush to a prepared tooth surface, letting the primer stand for 30 seconds, and then blowing the primer dry with compressed air. A small plastic straw with 3.68 mm inner-diameter and 2 to 3 mm in length is filled with uncured dental composite of the invention and seated on the dentin so as to form a post. The upper open end of the straw is covered with a thin film of cellophane. Gentle pressure (about 1–5 psi) is applied to the post through the cellophane with the tip of the handpiece of a MAX ® light curing unit (sold by L. D. Caulk Division of Dentsply International Inc.). The unit is activated and the composite is cured for 40 seconds. The specimens are stored in distilled water at 37° C. for 1 to 3 days and their posts are sheared on an INSTRON with 50 kg load and 5 mm/min. head speed. The shear bond strengths are calculated.

Coefficient of linear expansion is determined between 20° C. and 60° C. in air using an Orton R.R.C.(Westerville, Ohio) dilatometer (Model 1000D) at 3.00° C. per minute. Specimens are prepared according to the examples or, in the case of compatible materials (Prisma ® APH, Caulk Division/Dentsply, and Vitrebond, 3M Corporation), according to their directions for use.

EXAMPLE 5

A mixture suitable as a dental base is prepared by mixing 3.6 parts by weight of the powder formed as in Example 2 with 1 part by weight of the polymerizable liquid formed as in Example 1. Samples are polymerized using a Caulk MAX curing light. The composition has a flexural strength of 31.4 MPa and a flexural modulus of 4,903 MPa, tested according to ISO 4049.

EXAMPLE 6

A mixture useful as a dental restorative is prepared by mixing 4.0 parts by weight of the powder formed as in Example 2 with 1 part by weight of the polymerizable liquid of Example 1. The mixture is hardened and tested as in Example 4. The composition so prepared has a compressive strength of 26,629 psi by ISO 7489, diametral tensile strength of 4,859 psi by ADA 27, flexural strength of 47.7 MPa and flexural modulus of 4,118 MPa by ISO 4049, and a bond strength to human dentin of 1,097 psi.

EXAMPLE 7

A mixture suitable as a dental core build-up material is prepared by mixing 4.0 parts by weight of the powder formed as in Example 2 with 1 part by weight of the polymerizable liquid of Example 1. The product is hardened and tested as in Example 6. The product has essentially the same properties as in Example 6.

EXAMPLE 8

A blue dental core build-up material is prepared by mixing 4.0 parts by weight of the powder formed as in Example 3 with 1 part by weight of the polymerizable liquid formed as in Example 1. It is cured and tested as in Example 6 and exhibited essentially the same properties as Examples 6 and 7.

EXAMPLE 9

A dental cement is prepared according to the procedure of Example 4 except that 1.5 parts by weight powder prepared as in Example 2 is used, rather than 1.8 parts thereof.

The coefficients of linear expansion of the products of Examples 4 and 6 are summarized in Table 1 below in comparison with a competitive product—Vitrebond (3M Products Inc.) and Dentsply's Prisma APH light cured composite. Tooth enamel has a coefficient of thermal expansion of from 11 to 15 multiplied by $10^{-6}$ inch per inch per ° C.

TABLE 1

| | COEFFICIENT OF LINEAR EXPANSION (multiplied by $10^{-6}$ inch per inch per °C.) | | | |
|---|---|---|---|---|
| TEMP. °C. | EXAM- PLE 4 | EXAM- PLE 6 | PRISMA APH | VITREBOND |
| 25 | 17 | 28 | 66 | — |
| 37 | 26 | 32 | 52 | 57 |
| 45 | 33 | 34 | 59 | 80 |
| 55 | 42 | 36 | 61 | 76 |

The compositions of the powders of Examples 1–9 are summarized in Table 2.

TABLE 2

| POWDER | BLUE CORE BUILD-UP % | CEMENT/BASE LINER/RESTORATIVE CORE BUILD-UP % |
|---|---|---|
| Strontium fluoro-aluminosilicate glass | 99.2 | 79.2 |
| Ethyl 4-dimethyl-aminobenzoate | 0.8 | 0.8 |
| Barium alumino borosilicate glass | — | 20 |
| Inorganic pigments | trace | trace |

| | CEMENT | LINER | BASE | RESTORA-TIVE/CORE BUILD-UP |
|---|---|---|---|---|
| POWDER/ LIQUID RATIO | 1.5/1 | 1.80/1 | 3.6/1 | 4.0/1 |

Various alteration and modifications of this invention will be apparent to those skilled in the art without departing from the scope and spirit of this invention, and it should be understood that this invention is not limited to the illustrative embodiments set forth herein.

What is claimed is:

1. A dental composition, comprising:
   a) polyalkenoic acid,
   b) from about 10 to about 90 percent by weight elutable glass filler,
   c) effectively partially neutralized acid functional polymerizable organic ester,
   d) water,
   e) polymerizable monomer and/or prepolymer, and
   f) polymerization catalyst system,
   said elutable glass filler (b) being adapted to elute cations which are reactive with said polyalkenoic acid (a), and said monomer and/or prepolymer (e) being non-reactive with cations from the elutable glass filler.

2. The composition of claim 1 wherein said acid ester compound (c) is an ethylenically unsaturated organic phosphate ester or phosphonate.

3. The composition of claim 2 wherein said ethylenically unsaturated organic phosphoric acid ester is from about 20 to about 40 equivalent weight percent neutralized.

4. The composition of claim 1 wherein said acid ester compound is a dipentaerythritol pentacrylate phosphoric acid ester, pentaerythritol trimethacrylate phosphoric acid ester, glyceryl phosphate dimethacrylate or BIS-GMA diphosphonate.

5. The composition of claim 1 further comprising polyacrylic acid, hydroxyethyl methacrylate, triethylene glycol, dimethacrylate, and water.

6. The composition according to claim 1 wherein said polymerization catalyst system comprises a redox polymerization system effective at room temperature.

7. The composition according to claim 1 wherein said polymerization catalyst system comprises a free radical producing peroxide and reducing agent.

8. The composition according to claim 7 wherein said peroxide is benzoyl peroxide and said reducing agent is a tertiary amine or an organic sulfinate.

9. The composition according to claim 1 wherein the catalyst system is adapted to provide photopolymerization.

10. The composition according to claim 1 wherein the catalyst system comprises a redox polymerization system effective at room temperature in combination with a photopolymerization system.

11. The composition of claim 1 wherein said catalyst system comprises camphorquinone and a reducing agent.

12. The composition of claim 1 wherein the catalyst system comprises camphorquinone, ethyl 4-dimethylamino benzoate and a peroxide.

13. The composition according to claim 1 further comprising non-reactive fillers.

14. The composition according to claim 13 wherein said non-reactive glass filler is silica, silicates, or aluminosilicate glasses.

15. The composition according to claim 1 wherein said reactive filler comprises glasses containing cations having a valence of 2 or more and adapted to be elutable in said composition.

16. The composition of claim 1 further comprising ethyl 4-dimethylaminobenzoate.

17. The composition of claim 1 wherein said acid ester is of the general formula:

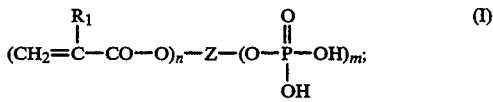

wherein $R_1$ is hydrogen, lower alkyl of from 1 to 5 carbons, halogen or CN radical; n and m are independently integers of 1 or greater, Z is an aliphatic, cycloaliphatic or aryl radical, having a carbon chain comprising at least 2 carbon atoms and 0 or more oxygen or sulfur atoms and having a valency of m+n and containing at least 2 carbon atoms.

18. The composition of claim 1 wherein said acid functional polymerizable organic ester further comprises a mixture of compounds of the general formulas:

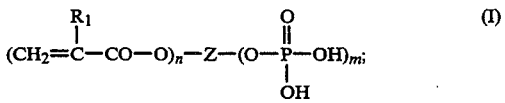

-continued

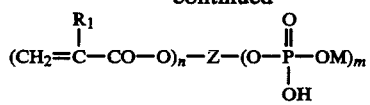

and

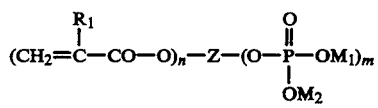

wherein $R_1$ is hydrogen, lower alkyl of from 1 to 5 carbons, halogen or CN radical; n and m are independently integers of 1 or greater, Z is an aliphatic, cycloaliphatic or aryl radical having a carbon chain comprising at least 2 carbon atoms and 0 or more oxygen or sulfur atoms and having a valency of m+n and M, $M_1$ and $M_2$ each is independently a cation.

19. The composition of claim 18 wherein from 20 to 40 equivalent weight percent of said mixture of compounds is neutralized by reaction with base.

20. The composition of claim 1 wherein said elutable filler comprises from about 10 to 90 percent by weight of said composition.

21. The composition of claim 1 wherein said elutable filler comprises from about 20 to 90 percent by weight of said composition.

22. The composition of claim 1 wherein said composition comprising polyacrylic acid, hydroxyethyl methacrylate, water, triethyleneglycoldimethacrylate, dipentaerythritolpentacrylate phosphoric acid ester, camphorquinone, and ethyl 4-dimethylaminobenzoate.

23. The composition of claim 1 wherein said dental composition comprises
(a) from 0.5 to 30 percent weight polyalkenoic acid,
(b) from 10 to 90 percent by weight elutable glass filler,
(c) from 1 to 60 percent by weight an acid functional polymerizable organic ester, and said acid functional polymerizable organic ester comprises a mixture of compounds of the general formulas:

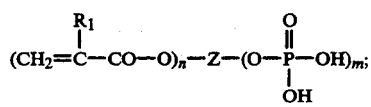

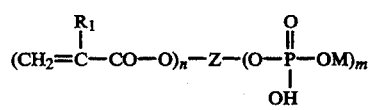

and

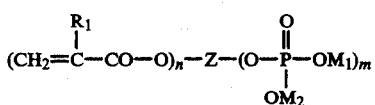

wherein $R_1$ is hydrogen, lower alkyl of from 1 to 5 carbons, halogen or CN radical; n and m are independently integers of 1 or greater, Z is an aliphatic, cycloaliphatic or aryl radical having a carbon chain comprising at least 2 carbon atoms and 0 or more oxygen or sulfur atoms and having a valency of m+n and M, $M_1$ and $M_2$ each is independently a cation, said mixture of compounds of general formulas I, II and III being formed by mixing from 20 to 40 equivalent weight percent of a base and said compounds at about pH 1,
(d) from 0.5 to 30 percent by weight water,
(e) from 1 to 60 percent by weight polymerizable monomer and/or prepolymer, and
(f) from 0.01 to 10 percent by weight polymerization catalyst system,
said elutable glass filler (b) being adapted to elute cations which are reactive with said polyalkenoic acid (a), and said monomer and/or prepolymer (e) being non-reactive with cations from the elutable glass filler, said composition being adapted to form a substantially radiopaque polymeric product.

24. The composition of claim 23 wherein said dental composition comprises
(a) from 0.5 to 20 percent weight polyalkenoic acid,
(b) from 20 to 90 percent by weight elutable glass filler,
(c) from 2 to 50 percent by weight of an acid functional polymerizable organic ester which is partially neutralized by addition of from 20 to 40 equivalent weight percent base,
(d) from 0.5 to 20 percent by weight water,
(e) from 2 to 50 percent by weight polymerizable monomer and/or prepolymer, and
(f) from 0.01 to 5 percent by weight polymerization catalyst system,
said elutable glass filler (b) being adapted to elute cations which are reactive with said polyalkenoic acid (a), and said monomer and/or prepolymer (e) being non-reactive with cations from the elutable glass filler, said composition being adapted to form a substantially radiopaque polymeric product.

25. The composition of claim 23 wherein said composition comprises from 1 to 60 percent by weight non-reactive filler.

26. The composition of claim 24 wherein said composition comprises from 4 to 40 percent by weight non-reactive filler.

27. The composition of claim 1 wherein said dental composition comprises
(a) from 0.5 to 10 percent weight polyalkenoic acid,
(b) from 30 to 90 percent by weight elutable glass filler,
(c) from 2 to 40 percent by weight an acid functional polymerizable organic esters, which are from 20 to 40 equivalent weight percent neutralized by mixing with a base,
(d) from 0.5 to 10 percent by weight water,
(e) from 5 to 40 percent by weight polymerizable monomer and/or prepolymer,
(f) from 0.01 to 4 percent by weight polymerization catalyst system, and
(g) from 4 to 30 percent by weight non-reactive filler,
said elutable glass filler (b) being adapted to elute cations which are reactive with said polyalkenoic acid (a), and said monomer and/or prepolymer (e) being non-reactive with cations from the elutable glass filler, said composition being adapted to form a substantially radiopaque polymeric product.

28. The composition of claim 27 wherein said acid functional polymerizable organic ester comprises from about 1 to 60 percent by weight of dipentaerythritol pentacrylate phosphoric acid of said composition.

29. A dental composition comprising
(a) a polymer of an α-β unsaturated carboxylic acid having a weight average molecular weight of 5,000 to 500,000, (b) a fluoroaluminosilicate glass powder having an average particle size of 0.02 to 50 μm and a specific gravity of 2.0 to 4.0 and capable of reacting with said polymer of an α-β unsaturated carboxylic acid having a weight average molecular weight of 5,000 to 500,000, (c) a polymerizable monomer and/or prepolymer, (d) a polymerization catalyst, (e) water, (f) ethylenically unsaturated organic acid, 20 to 40 equivalent weight percent salts of said ethylenically unsaturated organic acid, and (g) a reducing agent, said elutable glass filler (b) being adapted to elute cations which are reactive with said polyalkenoic acid (a), a substantial portion of said cations being strontium cations and said monomer and/or prepolymer (e) being non-reactive with cations from the elutable glass filler, said composition being adapted to form a substantially radiopaque polymeric product.

30. The composition of claim 29 further comprising at least one non-reactive filler.

31. A dental composition according to claim 29 wherein said non-reactive glass is further characterized by not forming a hardened coherent mass within 10 hours when combined with said α-β unsaturated polycarboxylic acid.

32. A dental composition according to claim 29 wherein said polymerizable monomer and/or prepolymer is further characterized as not forming a hardened coherent mass within 10 hours when combined with said non-reactive glass.

33. A dental composition comprising:

(a) 0.5 to 30 parts by weight of a polymer of an α-β unsaturated carboxylic acid having a weight average molecular weight of 5,000 to 500,000, (b) 10 to 90 parts by weight of a fluoroalumino-silicate glass powder having an average particle size of 0.02 to 50 μm and a specific gravity of 2.0 to 4.0 and capable of reacting with said polymer of an α-β unsaturated carboxylic acid having a weight average molecular weight of 5,000 to 500,000, (c) 1 to 60 parts by weight of a polymerizable monomer or prepolymer, (d) 0.5 to 30 parts by weight of water, (e) 1 to 60 parts by weight of ethylenically unsaturated organic acid and salts of said ethylenically unsaturated organic acid, said salts being 20 to 40 equivalent weight percent of said acid, (f) 0.01 to 5 parts by weight of a polymerization catalyst, and (g) 0.001 to 5 parts by weight of a reducing agent, said elutable glass filler (b) being adapted to elute cations which are reactive with said polyalkenoic acid (a), a substantial portion of said cations being strontium cations and said monomer and/or prepolymer (e) being non-reactive with cations from the elutable glass filler, said composition being adapted to form a substantially radiopaque polymeric product.

34. The composition of claim 33 further comprising 1 to 60 parts non-reactive glass powder.

35. A dental composition as claimed in claim 33 wherein said "polymer of an α-β unsaturated carboxylic acid having a weight average molecular weight of 5,000 to 500,000" is a co- or homopolymer containing at least one selected from the group consisting of acrylic acid, methacrylic acid, 2-chloroacrylic acid, 3-chloroacrylic acid, aconitic acid, mesaconic acid, maleic acid, itaconic acid, fumaric acid, glutaconic acid and citraconic acid.

36. A dental composition as claimed in claim 33 wherein said "polymer of an α-β unsaturated carboxylic acid having a weight average molecular weight of 5,000 to 500,000", is a co- or homopolymer containing acrylic and maleic acids.

37. A dental composition as claimed in claim 33 wherein said polymerizable unsaturated organic compound having at least one $CH_2=C(R1)-COO$ group wherein R1 is H or $CH_3$ is an ester of acrylic or methacrylic acid.

38. A dental composition as claimed in claim 33 wherein said fluoroaluminosilicate glass powder having an average particle size of 0.02 to 50 μm and a specific gravity of 2.0 to 4.0 and capable of reacting with said "polymer of an α-β unsaturated carboxylic acid having a weight average molecular weight of 5,000 to 500,000", contains $Al^{3+}$, $Si^{4+}$, $F^-$ and $O^{2-}$, as elutable cations and including further $Sr^{2+}$ and/or $Ca^{2+}$.

39. A dental composition as claimed in claim 33 wherein said "polymerization catalyst" is a photopolymerization catalyst.

40. A dental composition as claimed in claim 33 wherein said aluminosilicate glass powder having an average particle size of 0.02 to 50 μm and a specific gravity of 2.0 to 4.0 and capable of reacting with said polymer of an α-β unsaturated carboxylic acid having a weight average molecular weight of 5,000 to 500,000 is a fluoroaluminosilicate glass powder which is coated on its surface with an organic compound.

41. A two-paste dental composition comprising a first and a second paste, said first paste comprising a polyalkenoic acid, an acid functional polymerizable organic ester, and a non-reactive filler; said second paste, comprising a polymerizable monomer and/or prepolymer, cation elutable glass filler, and water, at least one of said first and second paste comprising a catalyst.

42. A method of treating a tooth consisting of dental compositions, comprising mixing a powder and polymerizable liquid in preselected proportions to form at least two dental compositions selected from the group consisting of cement, liner, base, restorative, core buildup, and pit and fissure sealant, and applying them to at least one tooth whereupon they are caused to harden wherein said dental compositions comprise a) polyalkenoic acid, b) elutable glass filler, c) an acid functional polymerizable organic ester, 20 to 40 equivalent weight percent salts of said acid functional polymerizable organic ester, d) water, e) polymerizable monomer and/or prepolymer, and f) polymerization catalyst system, said elutable glass filler (b) being adapted to elute strontium and fluoride cations which are reactive with said polyalkenoic acid (a) to form a substantially radiopaque polymeric product, and said monomer and/or prepolymer (e) being non-reactive with cations from the elutable glass filler.

43. The method of claim 42 wherein said powder comprises a glass-containing elutable cations of valence of 2 or more.

44. The method of claim 42 wherein said polymerizable liquid comprises polymerizable monomer and an acid ester compound.

45. The method of claim 42 wherein said polymerizable liquid comprises dipentaerythritol pentacrylate phosphoric acid ester.

46. The method of claim 42 wherein said powder and liquid are mixed in a ratio of from 0.5 to 6 parts by weight powder to 1 part by weight liquid.

47. A dental composition comprising a powder and liquid wherein said powder comprises
   (a) about 70–85 percent by weight strontium fluoroaluminosilicate glass,
   (b) about 0.7–0.9 percent by weight ethyl 4-dimethylaminobenzoate, and
   (c) about 15–30 percent by weight barium alumino borosilicate glass;
and said liquid comprises
   (a) about 6–8 percent by weight polyacrylic acid,
   (b) about 6–8 percent by weight water,
   (c) about 26–32 percent by weight hydroxyethyl-methacrylate,
   (d) about 26–32 percent by weight tetraethylene glycol dimethacrylate,
   (e) about 26–30 percent by weight dipentaerythritol pentacrylate phosphoric acid, dipentaerythritol pentacrylate phosphoric acid salts, said salts being 20 to 40 equivalent weight percent of said acid and
   (f) about 0.1–0.5 percent by weight camphorquinone, said elutable glass filler (b) being adapted to elute cations which are reactive with said polyalkenoic (a), a substantial portion of said cations being strontium and said monomer and/or prepolymer (e) being non-reactive with cations from the elutable glass filler, said composition being adapted to form a substantially radiopaque polymeric product.

48. A polymerizable liquid dental composition, comprising:
   14.2 parts by weight polyacrylic acid;
   28.5 parts by weight hydroxyethyl methacrylate;
   0.1 parts by weight butylate hydroxytoluene;
   28.5 parts by weight triethylene-glycol dimethacrylate;
   28.5 parts by weight partially neutralized dipentaerythritol pentacrylate phosphoric acid ester and
   0.2 parts by weight camphorquinone.

* * * * *